(12) United States Patent
El-Sherif et al.

(10) Patent No.: US 11,786,438 B2
(45) Date of Patent: Oct. 17, 2023

(54) UNIVERSAL FACIAL REJUVENATION TREATMENT SYSTEM (U-FRTS)

(71) Applicant: Skin Aesthetics Company, Berwyn, PA (US)

(72) Inventors: Mahmoud A. El-Sherif, Blue Bell, PA (US); Bruce Sheeran, Berwyn, PA (US)

(73) Assignee: Skin Aesthetics Inc., Berwyn, PA (US)

( * ) Notice: Subject to any disclaimer, the term of this patent is extended or adjusted under 35 U.S.C. 154(b) by 147 days.

(21) Appl. No.: 17/378,928

(22) Filed: Jul. 19, 2021

(65) Prior Publication Data
US 2023/0013440 A1  Jan. 19, 2023

(51) Int. Cl.
*A61H 7/00* (2006.01)

(52) U.S. Cl.
CPC ....... *A61H 7/005* (2013.01); *A61H 2201/105* (2013.01); *A61H 2205/022* (2013.01)

(58) Field of Classification Search
CPC .... A61M 2037/003; A61M 2037/0023; A61M 2037/0038; A61M 37/0015; A61B 2017/00747; A61H 7/005; A61H 2201/105; A61H 2205/022
See application file for complete search history.

(56) References Cited

U.S. PATENT DOCUMENTS

| 9,439,673 | B2* | 9/2016 | Austen | A61B 17/32053 |
| 2004/0087992 | A1* | 5/2004 | Gartstein | A61B 17/205 606/186 |
| 2018/0303515 | A1* | 10/2018 | Shadduck | A61B 17/320068 |

* cited by examiner

*Primary Examiner* — Anh T Dang
(74) *Attorney, Agent, or Firm* — Schott, P.C.

(57) ABSTRACT

A system for facial and skin treatment includes a universal skin exfoliating and rejuvenating system that uses dual-function plate mounted onto the front edge of the hand-held system in a multi-step process. One step used in the multi-step process includes of a microdermabrasion procedure using diamond-tipped wands fixed on a dual-function plate to cleanse and exfoliate dead skin that simultaneously removes the dead skin away. In another dual-function process, a plate equipped with micro-needles and skin care products is used to generate collagen for firmer toned skin. The micro-needles are fixed on moving parts or roller, to help with fine lines, wrinkles, and large pores. Also, a dual-function plate is used for skin massage and special serum treatment and application. The handheld system is equipped with a miniature vacuum pump, mini supply containers, and control parts to supply serums and skincare products to the dual-function plates.

11 Claims, 25 Drawing Sheets

Cross-sectional view A-A in FIG. 2

Cross-sectional view L-L of the dual-function plate shown in FIG. 7

Cross-sectional view K-K of the dual-function plate shown in FIG. 7, inside the plate holder 660

Cross-sectional view at the center of the micro-needling roller shown in FIG. 11

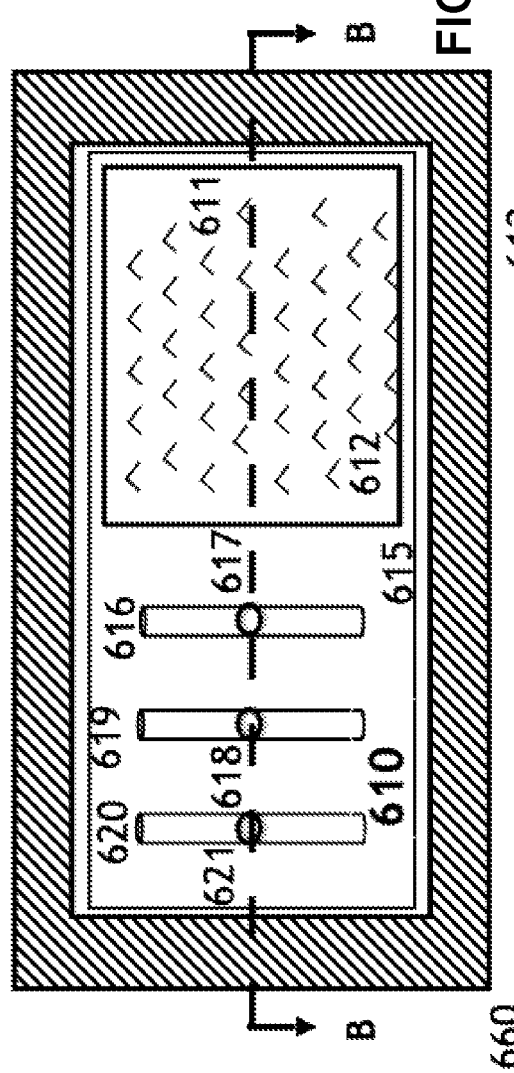
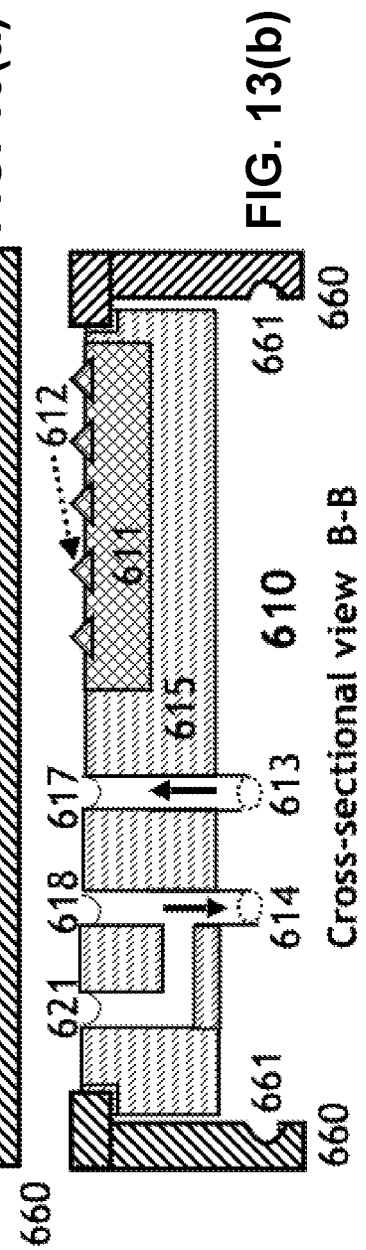
FIG. 13(a)
FIG. 13(b) Cross-sectional view B-B

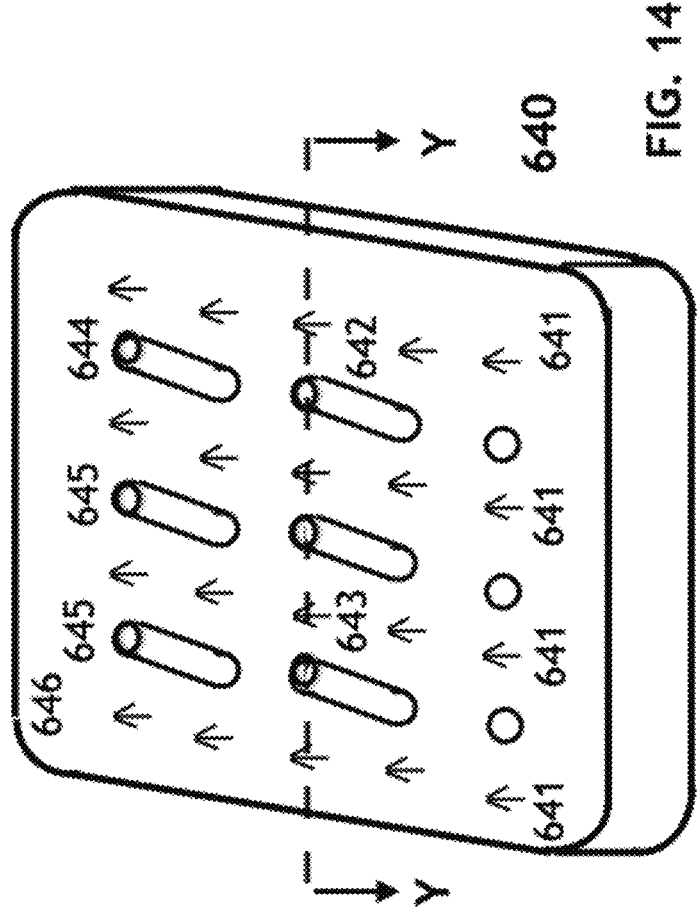

Cross-sectional view Y-Y of the dual-function plate shown in FIG. 14

Cross-Sectional view M-M in FIG. 16

A schematic cross-sectional view K-K of the base part 1580 in FIG. 20

Cross-sectional view N-N of the plate in FIG. 24

UNIVERSAL FACIAL REJUVENATION TREATMENT SYSTEM (U-FRTS)

FIELD OF THE INVENTION

This invention is in the field of facial and skin treatment, applying skin treatment processes with a compact semi-automatic hand-held system. It is designed for personal home application using specially designed parts/components for skin exfoliation and overall rejuvenation using approaches with wet microdermabrasion (hydradermabrasion) and micro-needling.

The invention relates to the field of devices for skin treatment and more specifically to a hand-held system capable of delivering a combination of skin exfoliating methods while stimulating collagen for overall smoother, firmer, and more toned skin.

BACKGROUND

Non-invasive aesthetic and cosmetic skin procedures have been on the rise for decades. Lasers, peels, injectables, microdermabrasion, and micro-needling have become a normal routine for skin treatment. Maintaining healthy looking skin is in demand. Patients seek out dermatologist and medical spas to get these treatments. Procedures can cost from a few hundred to a few thousand dollars. Combined procedures maximize skin treatment results.

Microdermabrasion is a procedure for removing dead cells from the outermost layer of the skin (epidermis) to reveal a younger and healthier looking appearance. Microdermabrasion can help clean out pores, reduce fine lines and wrinkles, and enhance overall skin tone. Microdermabrasion uses a mildly exfoliating instrument such as diamond tips to gently abrade the skin (similar to sand paper), removing the thicker, uneven outer layer, and then vacuuming it away from the skin. Diamond-tipped wands have been shown to be safe on patients with any skin condition. Because the outer thick dead layer of skin is removed, skin care serums and products are also readily absorbed by the skin. If there is too much build-up of dead skin, skin care products cannot effectively penetrate the skin to do their job.

Micro-needling can be used anywhere on the skin, however, most people will typically micro-needle their face and neck. This needling process perforates tiny channels into the skin which helps stimulate the growth of new collagen and skin tissue. This also allows better penetration and absorption of skincare products for smoother, firmer, and more even-toned skin. This may also help reduce fine lines and wrinkles, and large pores.

Light therapy technique or the photo-modulation of the tissue is a light therapy that involves transmitting light into the skin. Different color lights may be used to treat different types of skin conditions. For example, blue or violet light has been shown in some studies to reduce acne by killing certain bacteria in the pores. Photodynamic therapy (PDT) is another related technique. PDT involves applying a fluid containing a photosensitizing agent to the patient's skin. The photosensitizing agent is activated with a specific wavelength of light, such as ultraviolet light. This technique may reduce rough spots (actinic keratosis), brown spots (lentigo), and blotchy pigmentation. The most common type is solar lentigo, which typically arises in middle age and results from sun damage.

Radio frequency (RF) or microwave (MW) technique applies RF or MW energy directly to the skin. This involves thermally heating the collagen bundles in the skin. The heat causes collagen stimulation, which removes wrinkles.

Massage therapy is applied to stimulate the flow of blood and oxygen to improve the elasticity of the skin. Different types of moisturizers, lotions, or abrasive materials can be used during the mechanisms of massage therapy to stretch the skin, and provide openings for serums and skincare products to penetrate.

From this short overview, we can see that there are many options to rejuvenate skin. Some procedures and treatments are superficial, while others go much deeper; some have absolutely no recovery time, while others present with much longer recovery time. The procedures and treatments that one chooses is based on what they want to achieve. They may choose one treatment or a combination therapy. Lasers and RF procedures would be overseen by a medical doctor and are only available at a physician's office or a medical spa. The devices are expensive, ranging from $30,000 up to $150,000 and require extensive training. The cost for these procedures to patients is also quite expensive, ranging from a couple of hundred dollars to a few thousand dollars, and multiple sessions may be required.

Extensive use of skin treatment devices/systems has stimulated interest in developing a novel and simple system for skin treatment at home. The new system can provide a cost-effective alternative approach for skin treatment without visiting doctors' offices or medical spas.

While certain devices be used under supervision, others don't require FDA clearance or physicians' supervision and are ideal for home application. Alternatively, these home-use devices should be simple and not aggressive as in-office devices.

Therefore, there is a strong need for a novel and universal facial exfoliating and rejuvenating system for superficial skin treatment. The system has to be friendly, simple, and easy to use at home. The more the system is compact and in a handheld structure the more frequently it will be used at home.

SUMMARY OF THE EMBODIMENTS

The system described herein has all mentioned benefits and would be available at affordable prices, allowing people access to at-home treatment, without the need for a licensed health professional. It is also an ideal option and appropriate for people who don't have time to go to a health clinic or spa.

A novel handheld system for facial and skin rejuvenation treatment is developed. The handheld system is capable of delivering a combination of facial exfoliating methods while stimulating collagen for overall skin that is smoother, firmer, and more toned. The system is designed in a way to facilitate several processes simultaneously to maximize skin exfoliation and overall rejuvenation. This system is simple, and within a reasonable weight and compact size for personal use at home without the need for professional assistance or help. There will be no need to visit medical offices, licensed professionals, or health spas for this treatment. It is far less expensive and offers significant time savings by eliminating periodic/regular visits to professional offices and spas.

The invention relates to a skin therapy system. Specifically, it is a Universal Facial Rejuvenation Treatment System using a multi-process compact system. The system combines several skin therapy techniques including micro-needling, microdermabrasion, and massage therapy in a professional and simple application. This handheld system is equipped with a mini vacuum pump and number of mini containers, to provide serums and skincare products during application. The vacuum pump is used for moving fluids from containers to the skin surface and removal of dead skin through a number of flexible feeding tubes. A number of valves and switches are used for full control of the system operation.

In this invention, a micro-needling procedure is conducted in a more effective way by using a dual-function plate, combining a roller of micro-needles with a skin massaging while continuously applying skin care products. It is used as a cosmetic procedure for skin rejuvenation using mechanical micro-needling, by treating skin blemishes and skin imperfections such as scars or wrinkles. The use of micro-needles while simultaneously massaging with skin care products, maximizes the collagen generation for firmer toned skin. The micro-needles are fixed on a moving roller, and the roller is fixed onto one side of the dual-function plate, while the other side of the plate is used for skin massaging and supplies skin care products. This dual-function process helps in increasing the absorption and penetration of skincare products within the skin. Regardless of the skincare product used, it will be quickly absorbed into the skin. The skin then quickly tries to repair itself thereby producing more collagen. Combining the micro-needling process during massaging with a continuous supply of skincare products maximizes collagen stimulation, resulting in better reduction of fine lines, wrinkles, large pores, and can help in smoothing uneven skin texture. The micro-needling technique is used in a new and more effective way to fight the effects of aging and improving overall skin tone.

The design of this dual-function plate has two major components. The micro-needles section, and the skincare supplies and massaging section. In the micro-needles section, about 200-300 micro needles are fixed on a reasonable size roller. The size of the exposed part of each micro-needle is within the health and safety regulations, which can be 0.25 mm deep. The skincare supplies and massaging section, of this dual-function plate, has a plurality of fluid channels, which are formed in a special design to facilitate uniform spreading of skincare products across the skin surface, while continuously massaging the skin following each needle penetration step.

The plurality of fluid channels, on this section of the plate, are terminated next to the fluid supply opening/tube. The supply opening/tube may be positioned in the center of each fluid channel. This opening/tube is connected to the skincare container, wherein, the skincare serum or cream is pushed out from the container by pressure from the vacuum pump, thereby moving skincare supplies through a flexible tube to the fluid channels on the surface of this dual-process plate. The fluid channels may be uniformly distributed on the perimeter of the plate surface, or any special design for better uniform distribution of skincare products on the skin surface.

In an embodiment, a microdermabrasion procedure is used for skin exfoliation and removal of the superficial layer of dead skin cells. It is used in an effective way to fight the effects of aging. It is used as a cosmetic procedure for skin rejuvenation using mechanical abrasion for removal of all or part of the stratum corneum, and to treat skin blemishes or imperfections, such as scars or wrinkles. Microabrasion (or diamond peel) is a simple, straight forward, non-invasive procedure that revitalizes dull skin, shrinks large pores, reducing fine lines and wrinkles, acne scars, reduces pigment irregularities (hyperpigmentation), stretch marks, and age spots.

In an innovative design, diamond-tipped wands are used as a mildly abrasive instrument to gently sand the skin, removing the thicker, uneven outer layer. In a dual-function procedure, the removal of the dead skin layer is combined with massaging and spreading of special skincare products. Combining the removal of dead skin with skin massaging under continuous supplying of skincare products, maximizes the penetration of skincare products deeply into the skin outer layer. This type of skin rejuvenation is used to treat light scarring, wrinkles, fine lines, discoloration, sun damage, and stretch marks. Using a dual-process microdermabrasion operation, skin care products can penetrate deep into the skin, allowing the skin to build collagen and increase blood flow to the skin, which in turn yields a more youthful skin appearance.

In an embodiment of the system, the microdermabrasion operation includes a dual-process plate/disk/target. This plate has two main sections; one section is for diamond tips while the other section is for massaging with skincare products. This dual-process plate includes an abrading section formed on one side of the plate surface and a plurality of fluid channels is formed on the other side of the plate surface. The plurality of fluid channels are designed in a way to facilitate uniform distribution of cleaning fluids as well as collecting and removing of dead skin, whenever it is needed. The abrading section is formed by a large number of diamond tips distributed uniformly onto one side of the surface of the dual-process plate, and the massaging and fluid channels section has two openings connected to a couple of flexible tubes. One tube is for the continuous supply of cleaning fluids and/or skincare products, and the other tube is for dead skin and waste materials removal.

In an embodiment of the system, the microdermabrasion plate is designed in a special way, wherein the plurality of the fluid channels may be distributed on one section of the surface of the dual-process plate, between the diamond tip section and the vacuum opening/tube. The fluid channels are terminated on the plate surface next to a vacuum tube opening. The fluid channels may be uniformly distributed on the perimeter of the plate surface. The vacuum opening/tubes may be positioned in the center of the section of the fluid channels. One of the vacuum opening/tubes is connected to the cleaning fluids while the other is connected to a container for dead skin collection. A vacuum access opening is adapted to apply negative pressure to the skin surface, thereby removing dead skin in contact with the abrasive diamond tips.

In an embodiment of the system, the dual-process microdermabrasion plate is designed in a special way, where diamond-like bristles connected to the plate surface are distributed uniformly on the plate surface and overlapping with the fluid channels surrounding two passageway openings within the plate center. Wherein, one of the passageway openings is connected to a flexible tube for continuous supply of cleaning fluids and the other is for removal of abraded dead skin. The first passageway may provide fluids under pressure and the second passageway provides suction for dead skin removal. This dual-process approach is appropriate for most skin types because it is non-invasive and can effectively reduce wrinkles, acne, age spots, stretch marks, and more, in a reasonably short time.

In an embodiment of this invention, a special skin massaging procedure is designed in a way to maximize the skin brightness and rejuvenation, after the application and completion of the micro-needles and the microdermabrasion procedures. It is used for skin exfoliation in an effective way to fight the effects of aging on blood circulation. It may be used as a cosmetic procedure for skin rejuvenation using mechanical massaging, while simultaneously supplying skincare serum products.

In an embodiment of the system, the mechanical massaging procedure includes a dual-process plate. This plate has two main sections. One section has a specially shaped surface with uniform texture and solid bubbles for skin massaging and the other section is for continuous supply of skincare serum. The massaging section is not a smooth surface, and is formed by a large number of small surface solid bubbles distributed uniformly onto one side of the surface of the dual-process plate. The serum supply section has one opening connected to a flexible tube. This tube is connected to the serum container. The skincare serum is pumped from the container to the plate surface using pressured air from the vacuum pump. This side of the plate surface may have fluid channels designed in a way to facilitate uniform distribution of the skincare serum during the application of the mechanical massaging procedure.

In an embodiment of the system, the dual-process massaging plate is designed in a special way, wherein the small bubbles texture on the plate surface are distributed uniformly on the plate surface and overlapping with the plurality of fluid channels surrounding one passageway opening within the plate center. The passageway opening is connected to a flexible tube for continuous supply of skincare serum. The passageway provides serum or skin cream from the cream container while under vacuum pump pressure. This dual-process approach is the most appropriate way for effective skin massaging, for better blood circulation.

The combination of these three skin treatment procedures, dual-process micro-needling, dual-process microdermabrasion, and dual-process skin massaging, can provide the best expected results in skin exfoliation and rejuvenation, as recommended by dermatologists and skincare specialists for skin treatment. This hand-held compact system is easy to use at home in a simple and friendly way. It can provide tremendous advantages for daily use at home without the need for visiting a doctor office or a skincare spa.

The general description and the following detailed description are exemplary and explanatory only and are not restrictive of the invention, as defined in the appended claims. Other aspects of the present invention will be apparent to those skilled in the art view of the detailed description of the invention as provided herein.

BRIEF DESCRIPTION OF THE DRAWINGS

This summary is further understood when read in conjunction with the appended drawings. The features, aspects and advantages of the present invention are described with reference to drawings of certain preferred embodiments, which are intended to illustrate, but not to limit, the present invention. For the purpose of illustrating the invention, there are shown in the drawing's exemplary embodiments of the invention, however, the invention is not limited to the specific structural designs shown in the drawings. It is to be understood that these drawings are for the purpose of illustrating concepts of the present invention. In addition, the drawings are not necessarily drawn to scale. In the drawings:

FIGS. 13(a) and (b) show schematics of a dual-function microdermabrasion plate/disk/target, fixed inside the plate holder. The plate has two main sections: One has diamond tips distributed uniformly in this section, and the other section has a number of channels for continuous supply of cleaning liquids and removal of dead skin as well as leftover liquids. Also, the cross-sectional view B-B of the dual-function plate is shown fixed inside the plate holder.

FIG. 14 shows an embodiment of the dual-function microdermabrasion plate shown in FIG. 13, wherein the diamond tips and the cleaning supply channels are overlapping and distributed uniformly all over the plate surface.

DETAILED DESCRIPTION OF THE EMBODIMENTS

It should be understood that the configurations and/or approaches described herein are exemplary in nature, and that these specific embodiments or examples are not to be considered as the limits of the disclosed invention. The specific facial/skin treatment methods and systems described herein may represent one or more of any dual-function process. Additionally, the subject matter of the present disclosure includes any combinations and sub-combinations of various dual-function processes, as well as equivalents thereof. Also, the order of any described dual-function processes may be changed.

It is to be understood that this invention is not limited to the specific presented system, and that the terminology used herein is for the purpose of describing particular embodiments by way of example only, and is not intended to be limiting of the disclosed invention.

The present invention is on a handheld compact system for facial/skin therapy and universal skin rejuvenation, using dual-function processes, in order to maximize the skin rejuvenation treatment. The system combines several skin therapy techniques including microdermabrasion, micro-needling, and massage therapy using novel dual-function plates in a simple process and application. This handheld system may be equipped with a mini vacuum pump and a number of mini containers/bottles, for providing serums and skincare products during the application of any of the mechanical dual-function plates. The air pressure of the vacuum pump may be used to move fluids from mini containers to the skin surface, though a number of flexible tubes. Also, the pump vacuum pressure may be used as a suction tool for dead skin removal from the skin surface, through a flexible tube, which collects waste materials into a mini container/bottle. A number of valves and switches may be used for full control of the system operation and fluids movements. This invention is not limited to the specific designs and drawings presented herein. It is to be understood that these drawings are for the purpose of illustrating the concepts of the present invention, with no limitations, as presented next.

Figure 1:
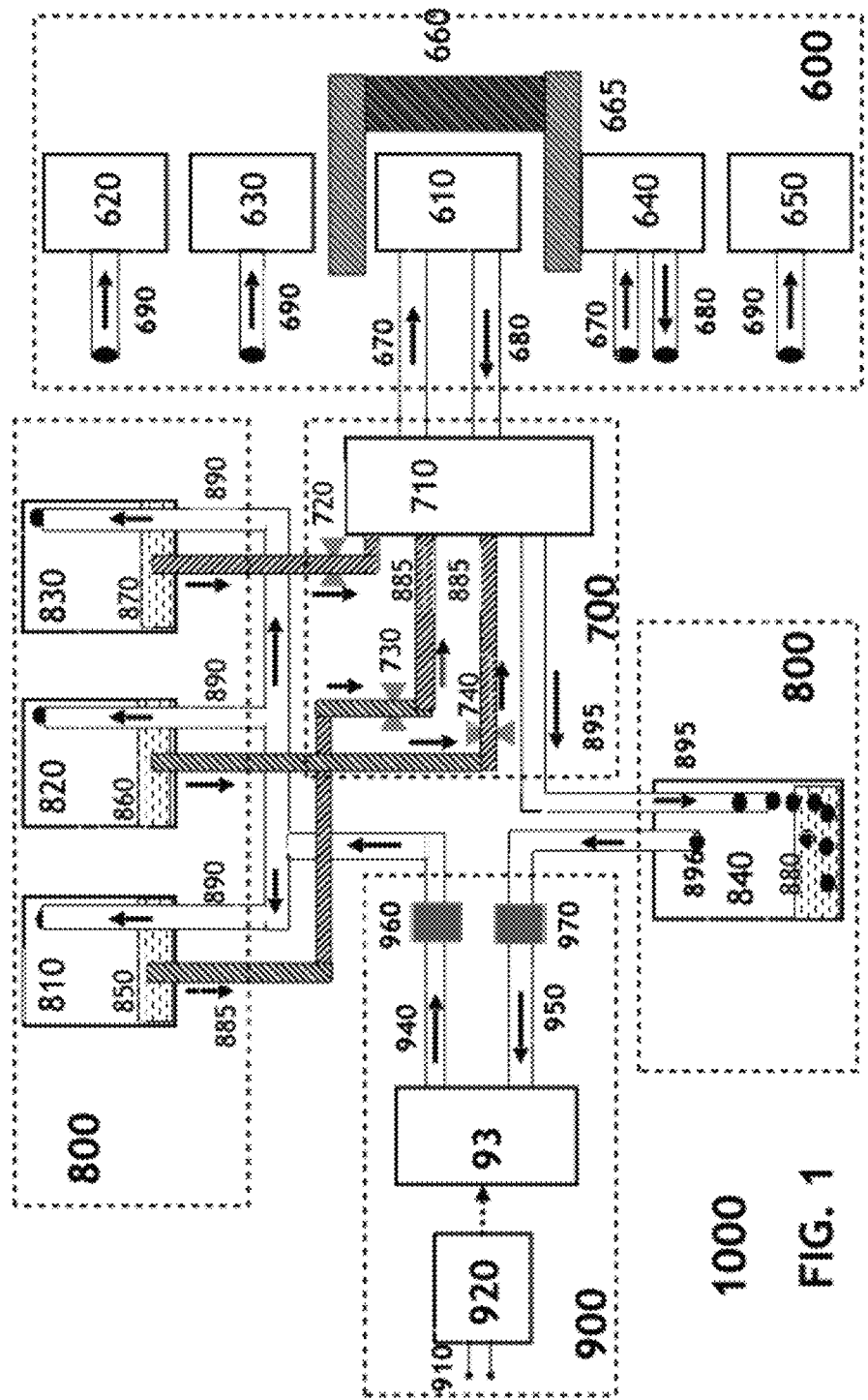
FIG. 1 shows the function/block diagram of the developed Universal Facial Rejuvenation Treatment System.

FIG. 1 shows an example of the functional/block diagram of the invented handheld compact system 1000, used for daily facial/skin treatment at home. The system is constructed of four major sections connected together in an easy and flexible way for different process applications. The section is mainly used as an interface contact section 600 with the patient's skin under treatment. The direct connection and control section 700 provides direct connections and mechanical control between the skin care supplies 800 and the skin interface section 600. A supply and product section 800 includes all the chemical supplies and skincare products, each in a mini container or bottle, as well as a container to collect waste materials, such as removed dead skin and waste cleaning liquids. The last section is the system's energy section 900. The energy section 900 may include a mini vacuum pump used to provide the pressure needed to pump the fluids and skincare products from the containers to the skin interface units, as well as vacuum suction of dead skin and cleaning liquids from the patient's skin to the bottle used to collect waste materials. Also, section 900 may include the required batteries and/or main supply adaptor for the vacuum pump operation, as well as On-Off switches for controlling the air flow from and to the vacuum pump.

The section 600 may include five dual-function/process plates 610, 620, 630, 640, and 650, wherein, each plate/disk/target has a different structure and special processing parameters for skin exfoliation and rejuvenation. The plate 610 is used for skin exfoliation using diamond tips for microdermabrasion technique, while massaging and removal of dead skin with cleaning fluids. This dual-function plate has two sections, one has a number of diamond tips and the other has a plurality of fluid channels. The fluid channels are connected through two flexible tubes 670 and 680 to two containers/bottles. The tube 670 is used to provide the cleaning fluids and the tube 680 is used for continuous suctioning and removal of dead skin material.

The second plate 620 may be used for skin rejuvenation using a micro-needling technique while massaging the skin with a skin serum and skincare products. The plate has two sections, one for micro-needling roller and the other has a plurality of fluid channels. The fluid channels are connected to the container of the skin serum and healing cream through a flexible tube 690. The third plate 630 is an embodiment of the plate 620 for skin micro-needling and rejuvenation, wherein the micro-needles section overlaps with the section of the fluid channels.

The fourth dual-function plate 640 is an embodiment of the plate for skin exfoliation 610 using a diamond tip section overlapping with the section of the fluid channels, which are connected through the two flexible tubes 670 and 680 to the cleaning fluid container and the dead skin collection container respectively. The fifth dual-function plate 650 is for massaging while providing continuously the required skin serum. It is connected to the container of the skin serum through the flexible tube 690.

The detailed differences between the five dual-function plates will be explained later within the system's schematic figure and the other figures of embodiment structural designs. A cap 660 and a mechanical coupling part 665 may be used in a simple and easy way to connect any of the listed dual-function plates to the system main body. Also, each of the dual-function plates is connected through one or two flexible tubes (670, 680, and 690) to one of the liquid supply containers of the skincare product in section 800, through the liquids control section 700.

Section 700 is designed in a way to provide the proper connection between any of the dual-function plates 610, 620, 630, 640, or 650 and one of the skin care products in any one of the fluids containers 810, 820, 830, or 840. The unit 710 in section 700 provides the proper mechanism to connect any of the flexible tubes 670, 680, or 690 from of the dual-function plate to the required fluid or waste materials container through the flexible tubes 885 and 895. The proper mechanism 710 connect the end of the tube 670 to the end of the tube 885, connected to the mini container 810 of the cleaning liquids. Also, this proper mechanism 710 connect the end of the tube 680 to the end of the tube 895, connected to the waste materials container 840. In addition, this mechanism 710 couples the end of the tube 690 to the end of the tube 885 connected to one of the two mini containers 820 or 830, which supplies the serum and skincare cream/products, with an option to switch between these two containers 820 and 830. Section 700 includes also a number of fluid valves/switches, such as 720, 730, and 740, to control the amount of the fluids (such as cleaning liquids, serum, or other skincare products) moving from the container/bottle to the skin interface plates.

Section 800 of the skin treatment system is the section for the skincare supplies. It has three containers/bottles/storage areas 810, 820, and 830 for saving skincare products 850, 860, and 870, such as serum and cream as well as the cleaning fluids that are used to clean the skin during the application of the microdermabrasion process and for continuous removal of dead skins. Air pressure is used, through the flexible tube 890, to pump the fluid/cream to one of the target plates through the flexible tube 885. Also in section 800, there is another container 840 that may be used to collect dead skins 880 and the used cleaning fluids 880 from the dual-function plate, through the flexible tube 895. Vacuum suction is applied, through the flexible tube 896, from the vacuum pump to the container 840 to facilitate continuous suction of dead skin from the surface of the microdermabrasion's plate.

Section 900 is mainly constructed of a mini vacuum pump 930 that is used to generate the required air pressure for moving any of the fluids from the container to the dual-function plate through the flexible tube 940 and the one-way air valve 960. Also, the mini vacuum pump 930 is used for dead skin suction from the surface of the microdermabrasion plate 610 or 640 through the flexible tube 680 to the container 840. The air suction is applied by the vacuum pump through the flexible tube 950 and the one-way valve 970. The mini vacuum pump is operated by a DC current generated by the adapter 920, which is connected to the main supply 910. Also, the unit 920 includes a set of DC batteries so the skin treatment system can be used away from the home's main supply.

Figure 2:
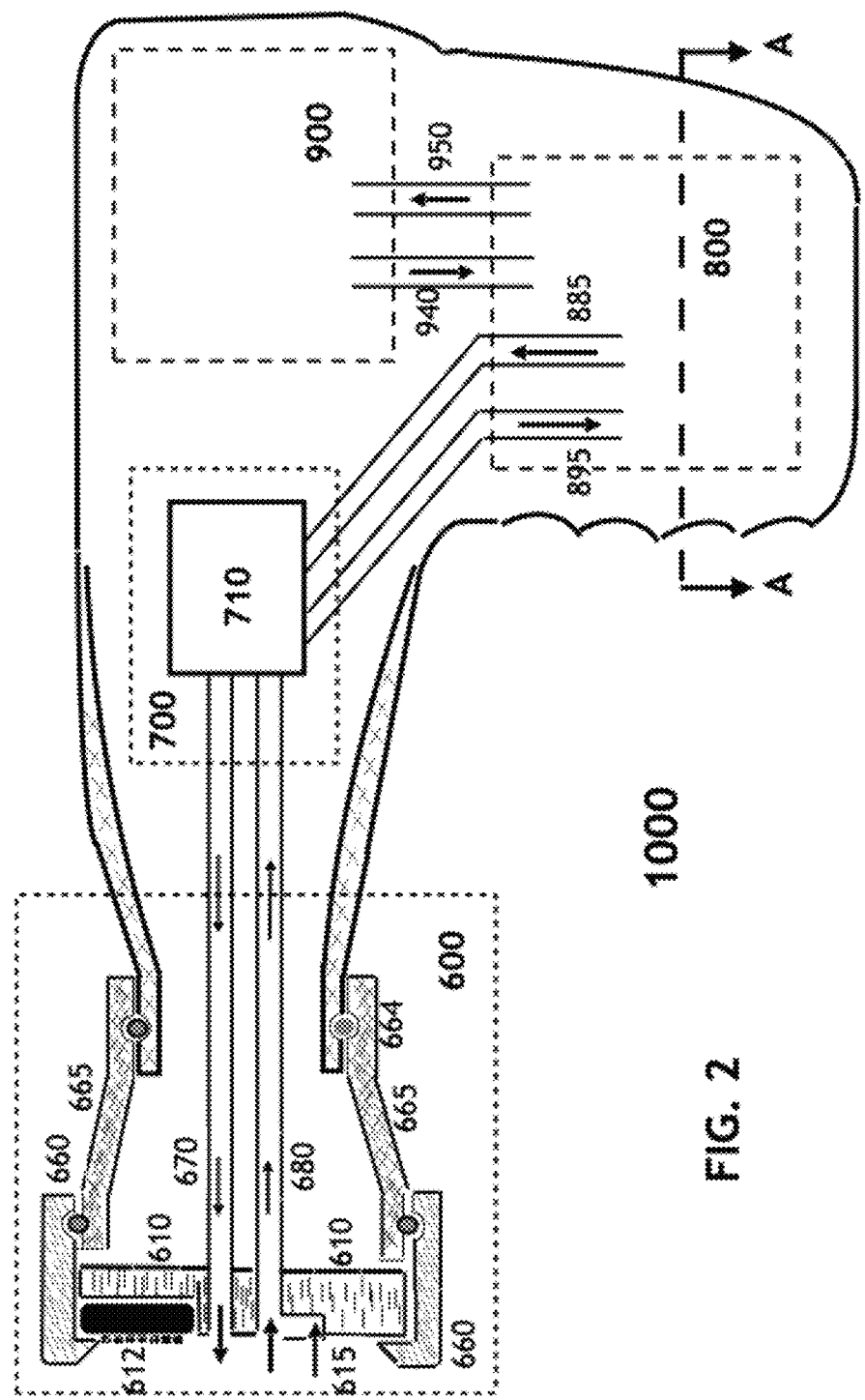
FIG. 2 is a schematic of the developed handheld Universal Facial Rejuvenation Treatment System, wherein the components are designed in a reasonably small and compact structure to be integrated together in a handheld system.

FIG. 2 is a schematic of the invented handheld Universal Facial Rejuvenation Treatment System 1000, wherein all the components are designed in a reasonably small size and compact structure to be integrated together in a light weight handheld system 1000. The system is designed in a way to facilitate the movement of the saved fluids and skincare products from section 800 to the patient's skin, using pressure and vacuum generated by a mini vacuum pump 930 located in section 900. Section 900 has a mini vacuum pump 930 and a set of batteries for the operation of the vacuum pump. Also, section 900 has an adapter for direct connect to the main supply. The outputs of the vacuum pump, of positive and negative pressures, are connected through the two flexible plastic tubes 940 and 950, to the supply containers/bottles in section 800 to manipulate the motion of the fluids from and to the containers. Section 800 is constructed of a number of mini containers/bottles used for saving the skin serum and other skincare supplies, as well as the container used for collecting dead skin material resulting from the application of the microdermabrasion process. Any of the containers in section 800 is connected to the dual-function plates through the control section 700. Two flexible tubes 885 and 895 may be used in moving the fluids from (or to) any of the containers to the unit 710, which is used to provide the proper mechanisms to connect the flexible tubes 885 and 895 from one of the containers to the other two flexible tubes 670 and 680 connected to the target plate 610. Section 600 is designed in a simple way to facilitate the quick and easy replacement/changing of the dual-function plate 610 with one of the other available plates for application of a different skin treatment process. Any used dual-function plate, such as 610, will be connected to the main body of the handheld system through the mechanical adapter 665, which will connect/fasten/lock the cap 660 with the main body of the handheld system. The connection between the three pieces can be achieved by using the solid rubber cord 664, in a clip-on technique, as an example, however other removable connector techniques such as screws can also be used. The dual-function target/plate 610 presented in this schematic figure is for the microdermabrasion process, which is one of the main processing plates for the skin treatment having two main sections 612 and 615. The section 612 is the diamond tips abrasion section, and the 615 section is for continuous supply of the cleaning liquids and removal of dead skin during the application of the abrasion process.

Figure 3:
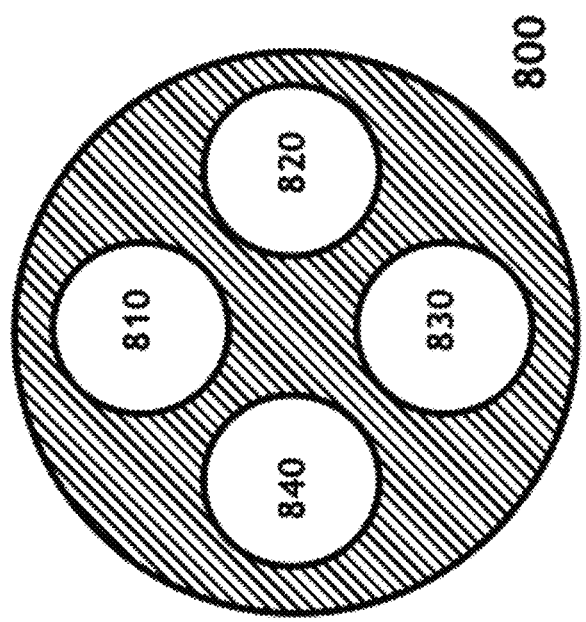
FIG. 3 shows the cross-sectional view A-A of the base of the handheld compact system shown in FIG. 2, wherein all the containers of liquids and creams are saved.

FIG. 3 shows the cross-sectional view A-A of the base 800 of the handheld skin treatment system 1000 shown in FIG. 2. The figure shows the cross-sectional area of the containers 810, 820, and 830, wherein the skincare supplies, such as serum, cream, and cleaning liquids are saved. Also, it shows the cross-sectional area of the container 840, which is used to collect the dead skin and the waste of cleaning liquid during the application of the microdermabrasion process.

Figure 4:
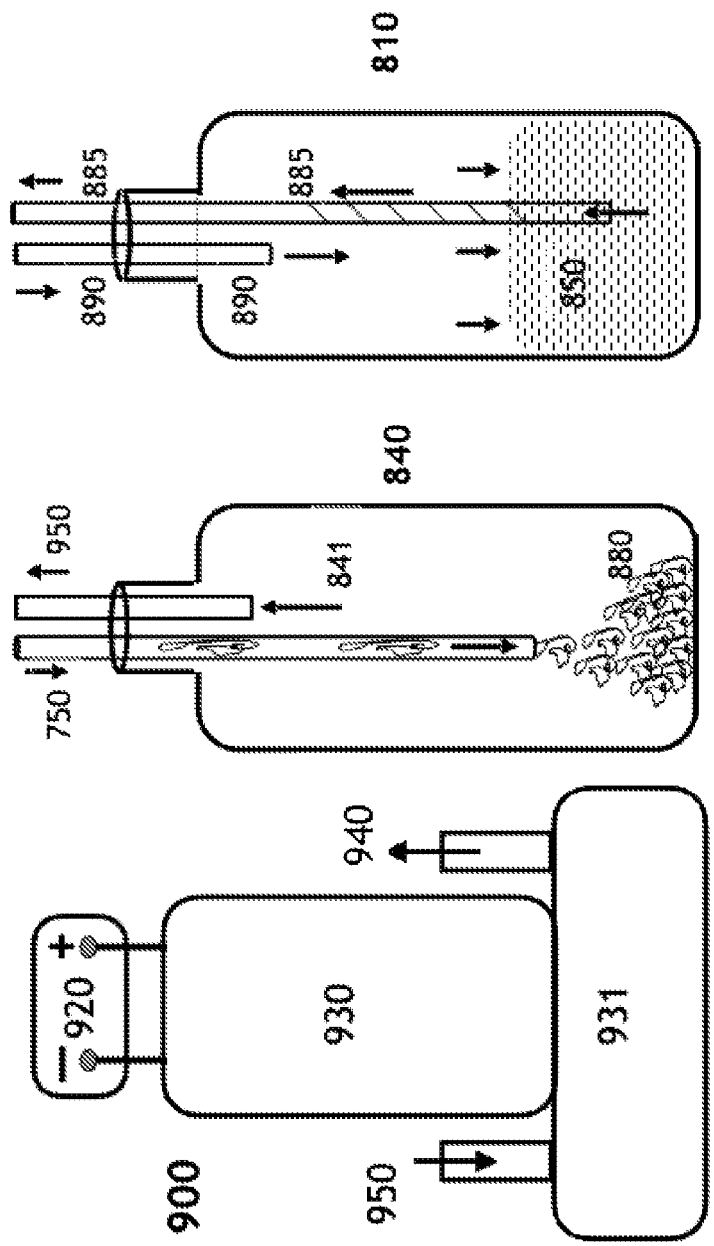
FIGS. 4(a)-(c) show schematics of three major components of the handheld system, wherein; (a) is a mini vacuum pump, connected to the required electricity/energy source, (b) is a mini container (or bottle) for collecting dead skin and cleaning liquids, and (c) is a mini container (or bottle) for saving serum or skincare products.

FIGS. 4(*a*)-(*c*) show schematics of three major components of the handheld system, wherein FIG. 4(*a*) shows a mini vacuum pump 930 sitting on a mini air chamber/cavity 931 for air circulation, wherein the air chamber has two openings for air output and input which are connected to the other system components through two flexible tubes 940 and 950 respectively. Also, the mini vacuum pump is connected to a set of batteries 920 and/or an adaptor as the required electricity/energy source for the mini pump. The mini vacuum pump can be powered by using one or more power sources. For example, in some embodiments, a battery (e.g., disposable, rechargeable, etc.), an AC power source (e.g., with or without a transformer) or any other power device or source can be connected, attached, or otherwise supplied to the desired component or subcomponent of the treatment system. In addition, the system can include one or more controllers, electrical and/or instrumentation connections, ports and/or the like as desired or required for the proper operation of the treatment system. According to one embodiment, the mini pump assembly 900 illustrated in FIG. 4(a) is configured to include a rechargeable battery.

FIG. 4(b) shows a mini storage container or bottle 840, which is used for collecting dead skin 880 and waste/cleaning liquids 880. The vacuum (negative) pressure applied to this container 840, through the tube 950 (which is connected to the vacuum pump) to generate the required suction/vacuum pressure at the surface of the dual-function plate next to skin surface and collects the dead skin and waste materials (abraded skin particles and fluids) through the connecting tube 750 to the waste container 840, which is well sealed from atmospheric pressure, at the container's bottle-neck.

FIG. 4(c) shows one of the skin product storage containers 810, which is used to save skincare products 850 used with the dual-function plates. The saved skincare products 850 are delivered from the container 810 to the dual-function plate by pumping higher air pressure to the container through the connecting tube 890, which is connected to the output of the vacuum pump. This higher air pressure moves the fluids from inside the container through the tube 885 to the surface of the dual-function plate. The flow rate of the liquid is adjustable by controlling the pressure of the air flow delivered to the container, while the container bottle-neck is well sealed to maintain the air pressure under full control.

Figure 5:
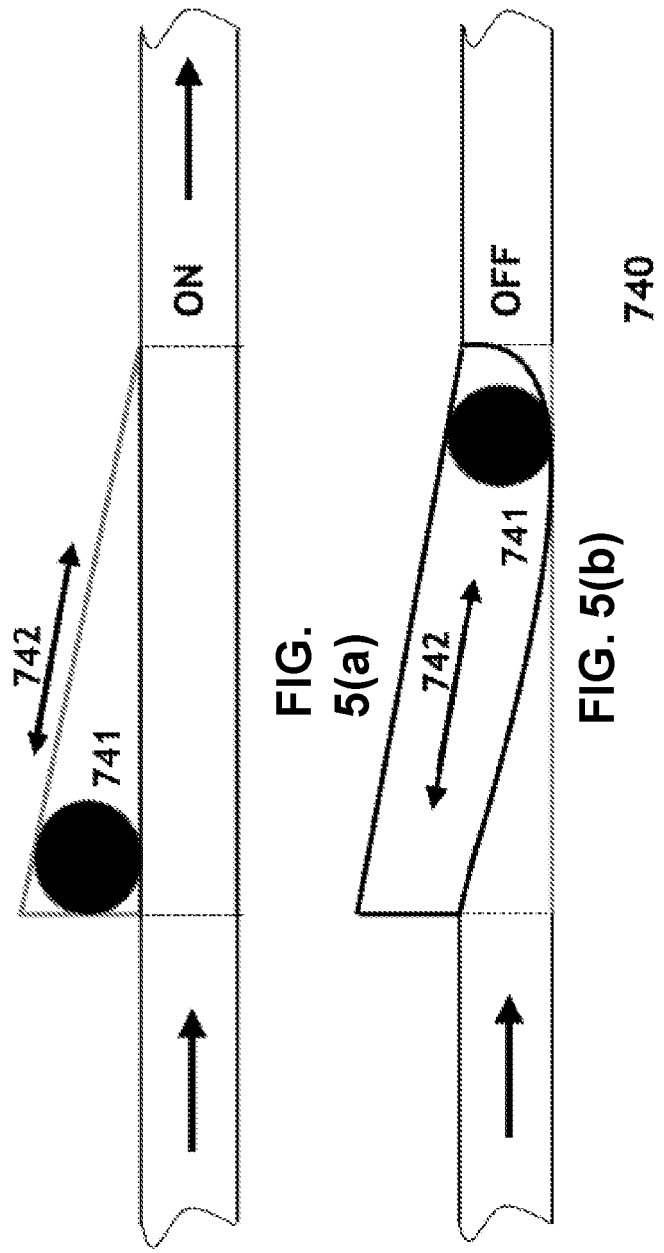
FIGS. 5(a) and 5(b) are schematics of a mechanical valve, for controlling the flow of the skin serum or cream from the container to the skin area, shown in the two extreme ON and OFF positions.
Figure 6:
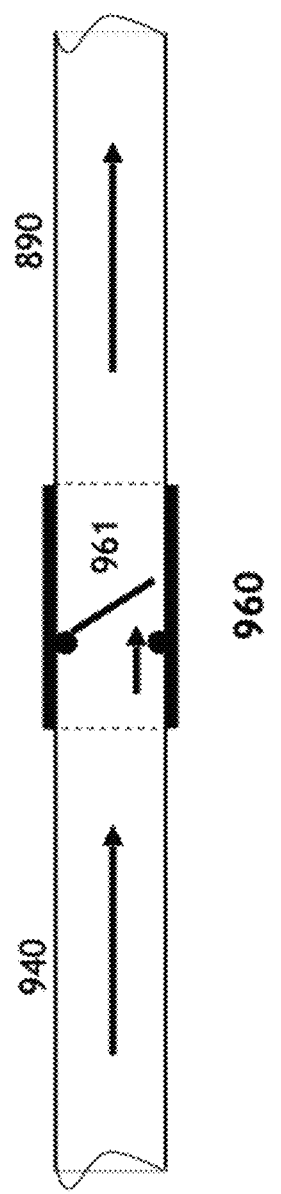
FIG. 6 shows an air switch to pass the air from or to the mini vacuum pump, as a one-way switch.

FIGS. 5(a) and 5(b) present a schematic of an example of a mechanical valve 740 that is used for controlling the flow rate of the serum and skincare products from any container to the surface of the dual-function plate that is in contact with the patient's skin. The mechanical valve is shown in the two extreme positions, FIGS. 5(a) the ON position and 5(b) the OFF position. The control hand 741 can be moved left or right on the motion adjustable track 742 based on the required flow rate of the liquid/cream under use. FIG. 6 shows a schematic of the one-way switch 960. The switch is connected to the output of the mini vacuum pump through the flexible tube 940. The output air will continue only in the same direction based on the position of the leaver/door 961 which is either open or closed. This air flow continues under certain pressure through the flexible tube 890 to the fluid container, and is used to pump the liquids from the container to the dual-function plate. A similar switch 970 is used in an opposite position to control the air flow in one direction at the input of the mini vacuum pump, as shown in FIG. 1. This second switch controls the vacuum pressure in the container 840, which is used to collect dead skin by applying a suction vacuum pressure at the surface of the microdermabrasion plate at the skin surface.

Figure 7:
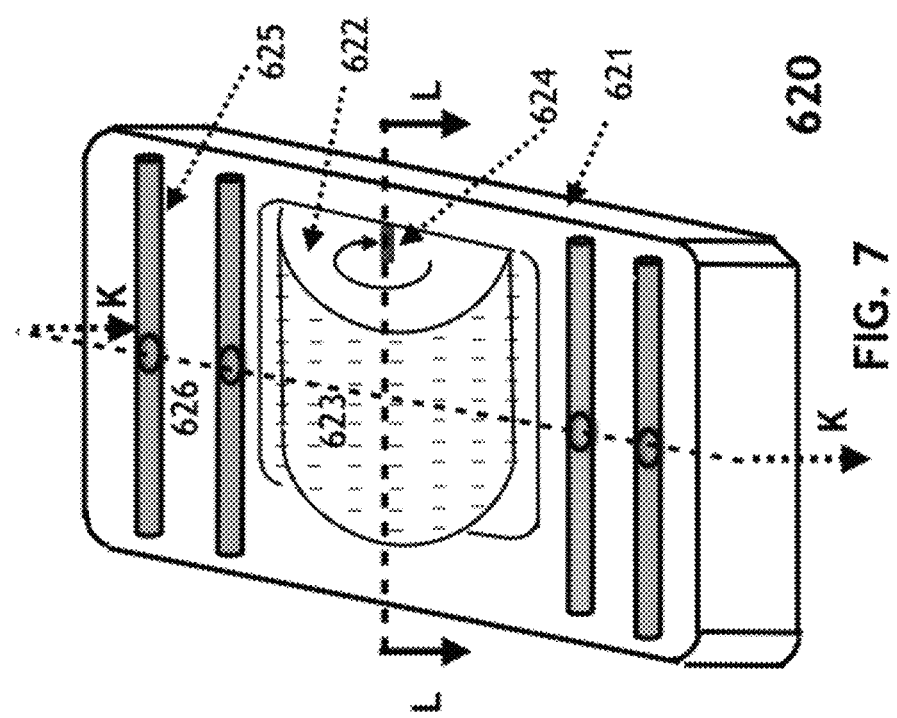
FIG. 7 is a schematic of a skin dual-function exfoliation plate, combining a roller for skin micro-needling and a plurality of fluid channels for the continuous supply of skincare products and massaging, during the application of the micro-needling process.

FIG. 7 is a schematic of a dual-function skin exfoliation plate/target 620, designed of a common base 621 that has two major sections; one is for a skin micro-needling roller 622, and the other is for skin massaging with healing cream and skincare products provided simultaneously during needling, through fluid channels 625 designed in a way to facilitate uniform distribution of the skincare serum during the application of the micro-needle's roller. Each fluid channel has an opening 626 connected through a flexible tube to one of the serum/cream container. The roller of the micro-needles has a large number of micro needles 623 which are fixed onto the surface of the roller in a special uniform distribution to maximize the interaction of each needle with the skin surface. Each of the micro needles may have a limited exposure length 0.25 mm, based on standard safety regulations. These micro needles may be used to create 0.25 mm superficial puncture holes that extend across and through the surface of the skin. This needling procedure, that perforates tiny channels into the skin, facilitates the immediate passage and absorption of the healing serum and skincare products into the outer skin layer. The roller is positioned under free rotation conditions around the axis 624, which is fixed in position with respect to the base of the dual-function plate 621. The micro needles, which may be fixed onto the cylindrical surface of the roller, create vertical micro perforations into the epidermis and the top layer of the stratum corneum. Hundreds of tiny channels are created through the top layer of the skin which facilitate the passage and absorption of skincare products. This dual-function process stimulates blood flow to the surface, delivers product and stimulates collagen re-growth, while gently exfoliating skin cells which contributes directly to the removal of scaring or premature skin aging signs, such as wrinkles and stretch marks. The cross-sectional view L-L of the micro-needling roller is shown in FIG. 8, and the longitudinal cross-sectional view K-K is shown in FIG. 9.

Figure 8:
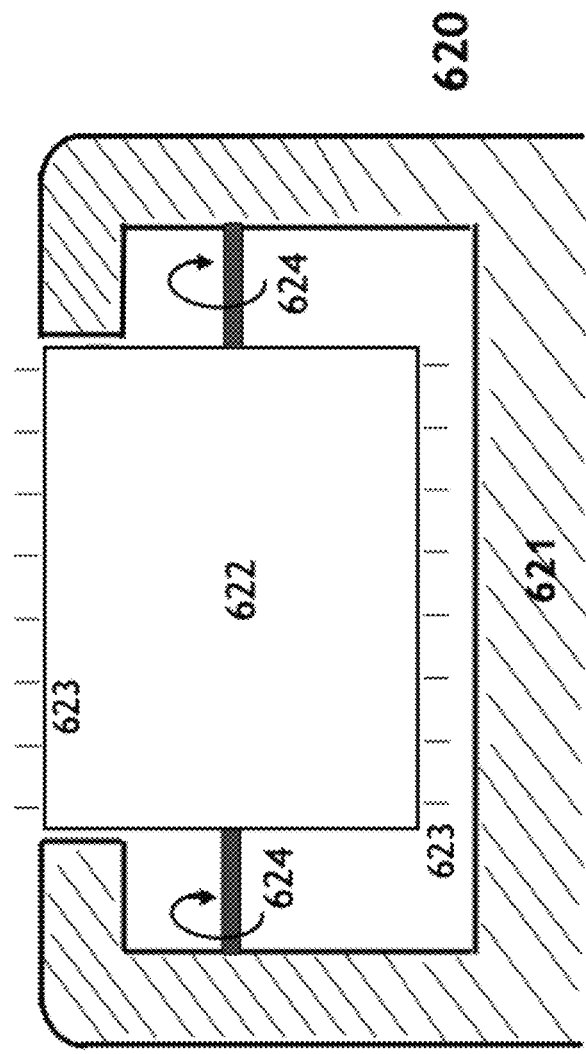
FIG. 8 is a schematic of the transverse cross-sectional view L-L of the dual-function plate shown in FIG. 7, at the location of roller that is fixed into the plate sides for free rotation.

FIG. 8 is a schematic of the cross-sectional view L-L of the dual-function plate 620 shown in FIG. 7, along the center axis/plane of the micro-needling roller. The figure shows the cross-sectional view of the base 621 of the dual-function plate 620, wherein the cross-sectional plane of the micro-needling roller 622 is shown connected to the axis 624, which is positioned into the sides of the base 621 for smooth and free rotation of the roller. The figure also shows the exposure of the micro-needles 623 outside the plate surface for easy penetration into the skin outer layer during the free rotation of the roller. The needle height exposed outside the plate surface is 0.25 mm which is based on cosmetic safety regulations.

Figure 9:
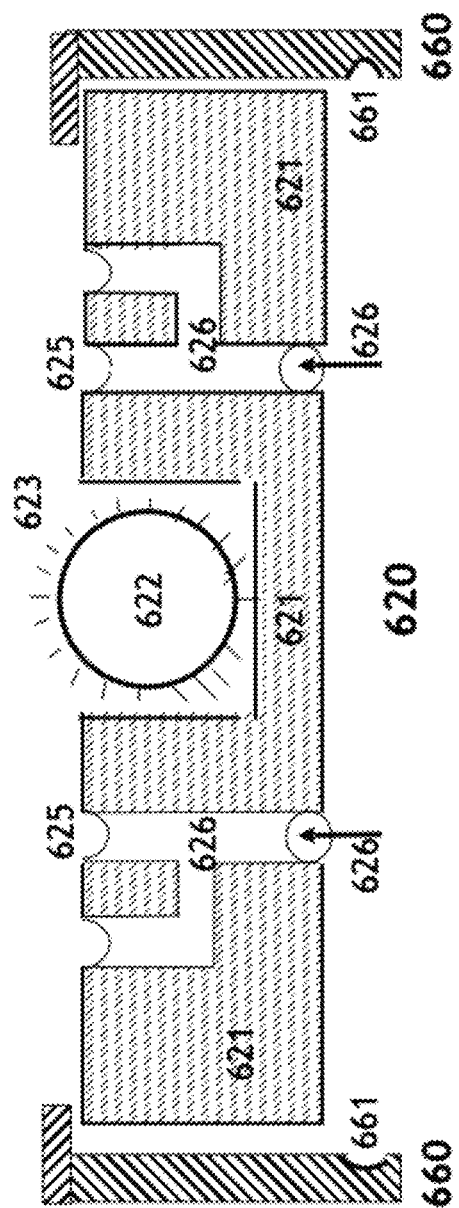
FIG. 9 is a schematic of the longitudinal cross-sectional view K-K of the dual-function plate in FIG. 7, shown inside the external plate holder 660.

FIG. 9 is a schematic of the longitudinal cross-sectional view K-K of the dual-function plate shown in FIG. 7, inside the external plate holder 660. It shows the circular cross-section of the cylindrical roller 622 in the center of the dual-function plate 621, wherein micro-needles 623 are shown fixed into the outer surface of the roller. Also FIG. 9 shows, from the left and right of the micro-needle roller, the cross-sectional view of the fluid channels 625, wherein the fluid channels 625 are connected to the containers of the serum and healing cream through the feeding tubes 626. The dual-function plate is always fixed in position with respect to the skin treatment system by a plate holder 660, wherein FIG. 9 shows the cross-sectional view of the holder 660. Wherein the holder has a small grove/channel 661 used in attaching/fixing the holder to the skin treatment system.

Figures 10A, 10B:
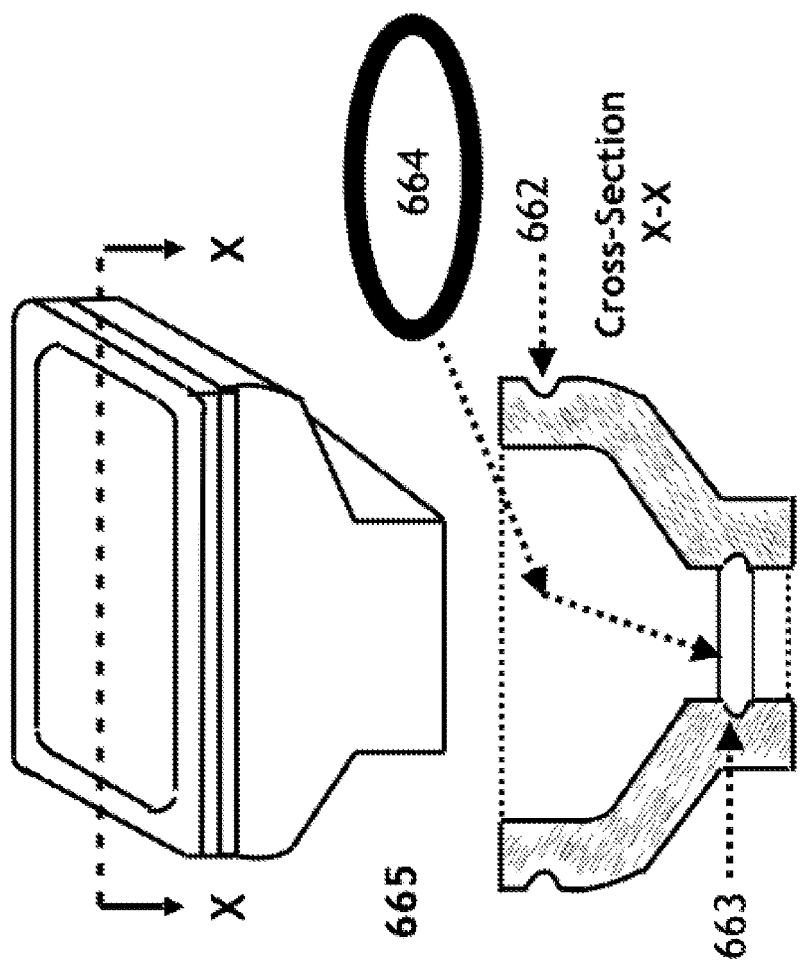
FIGS. 10(a) and 10(b) are schematics of the mechanical coupling part/component 10(a) that is used to connect a dual-function plate to the system body, by using the shown solid elastic rubber ring cord. Also, the schematic of the cross-sectional area X-X of this part is shown in 10(b).

FIGS. 10(a) and 10(b) is a schematic of the mechanical coupling part/component (FIG. 10(a)) 665, which is used to connect the holder of the dual-function plate to the body of the skin treatment system, by using the solid elastic rubber ring cord 664. The solid elastic rubber ring cord is used to clip-on the holder of any dual-function plate to the mechanical coupling part/component, as well as coupling the mechanical coupling part to the main body of the system. Also, the schematic of the cross-sectional view X-X of this mechanical coupling part 665 is shown in FIG. 10(b). The mechanical coupling part 665 has one groove/channel 662 from outside for coupling with the holder of the dual-function plate using the rubber ring 664 to clip-on/coupling the two parts, using the rubber ring cord 664. Also, the mechanical coupling part 665 has another groove/channel 663 from inside for direct clip-on/coupling to the skin treatment system using a similar, but different in size, rubber ring cord 664.

Figure 11:
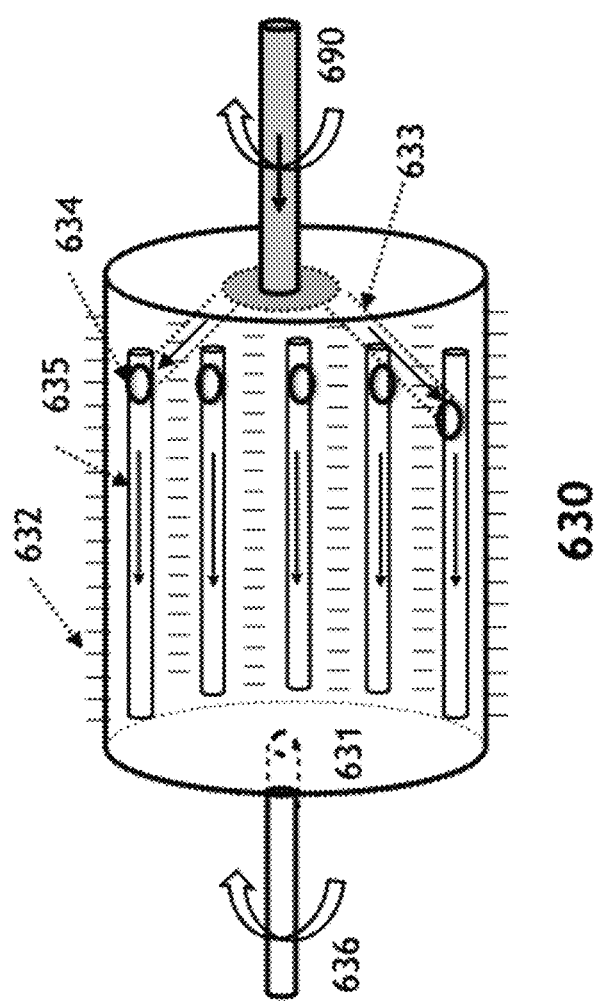
FIG. 11 is a schematic of an embodiment of the skin dual-function exfoliation plate shown in FIG. 7, wherein, the micro-needling roller continuously provides the skin healing serum from channels localized on the roller surface, in parallel to the lines of the fixed micro-needles.

FIG. 11 illustrates an embodiment of the dual-function plate 630 of the plate 620 shown in FIG. 7. In FIG. 11 the assembly of the dual-function plate 630 shows a different structure of the two major components, wherein the micro-needles 632 and the fluid channels 635 are overlapping in positions. The roller body 631 comprises the micro-needles 632 arranged in a number of lines and the fluid channels 635 are filling the gap between each two micro-needle lines. The micro-needles are arranged in lines of approximately 10-12 micro-needles between each two parallel fluid channels. The supply of the healing cream and skincare serum are provided from the containers of the cream or the serum through the flexible tube 690 to the tubes 633 going through the body of the roller, then through the openings 634 to the fluid channels 635. The serum and skincare products are provided continuously from the fluid channels on the roller next to micro-needles during the needling process. This can help in speeding up the healing action and maximize the skin exfoliation process. This is done continuously while the micro-needling roller is rotating around the supporting axis 636.

Figure 12:
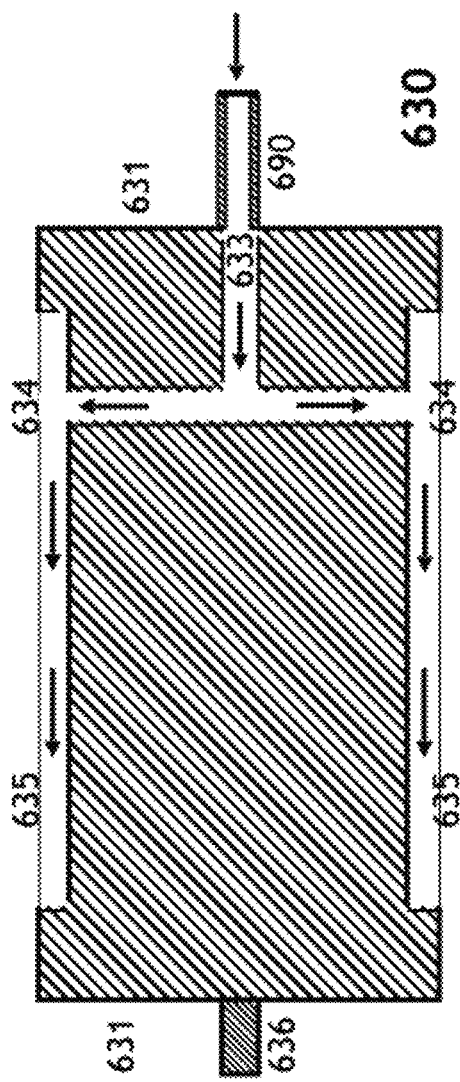
FIG. 12 shows a longitudinal cross-sectional view at the center of the dual-function micro-needles roller, showing samples of channels for continuous delivery of the serum and other skin products.

FIG. 12 is a schematic of the cross-sectional view at the center of the micro-needling roller 630 shown in FIG. 11, wherein, the roller cross-section is taken at the center line of two parallel fluid channels 635. FIG. 12 shows the skincare fluid/supply is pumped from the fluid containers through the flexible tube 690 to the roller body 631. This continues through the internal fixed tubes 633, going through the body of the roller and through the opening 634 to the fluid channels 635. The roller is fixed onto the sides of the plate for free rotation around the axis 636.

FIGS. 13(a) and (b) show schematics of the dual-function plate 610 according to another embodiment. In the depicted plate, the assembly shown includes the main components of a dual-function plate used for skin treatment, wherein, the application of the microdermabrasion procedure is used for skin rejuvenation. FIG. 13a shows the plane view of the plate inside the plate holder 660, as well as the cross-sectional view B-B (FIG. 13(b)) of the plate fixed inside the plate holder 660. In FIG. 13(a) the dual-function plate 610 is constructed of a common base 615, which has two major sections. The first one has a smaller plate 611, which is physically attached to the common base 615 for direct application of the microdermabrasion procedure to the skin. This small plate 611 is used to carry a large number of diamond tips 612 fixed onto the surface of the small plate 611, used for the microdermabrasion procedure. The microdermabrasion procedure uses medical-grade diamond-tips to exfoliate and suction away dead skin cells (and other impurities) that can clog pores, leading to inflammation, spots, blackheads and acne breakouts. The second section of the common base 615 is used for skin massaging and cleaning, using the proper cleaning liquids, and for collecting and removing the waste liquids and dead skins resulting from the application of the microdermabrasion procedure. The channel 616 is used to supply the cleaning liquids received from the liquid container through the opening 617 into the channel 616. At the same time, the waste liquids and the dead skin debris are collected from the skin surface to the channels 619 and 620 by vacuum suction applied by the vacuum pump. The waste materials (abraded skin particles and cleaning fluids) are pulled out from the waste channels through the openings 618 and 621 to the waste collection container.

FIG. 13(b) is a schematic of the cross-sectional view B-B of the dual-function plate 610 and the plate holder 660 shown in FIG. 13(a). The plate has a common base 615, which has two operating sections. The first section is for the application of the microdermabrasion procedure. Wherein, a large number of diamond tips 612 fixed on a small plate 611 are used in applying the microdermabrasion procedure to exfoliate dead cells from the skin surface. The second section is used for skin massaging and continuously cleaning waste materials during the microdermabrasion process, designed to suction away all impurities that can clog pores, leading to inflammation, blackheads and acne breakouts. Special cleaning liquid is pumped out of the container through a flexible tube to the fixed tube 613, embedded inside the dual-function plate and through the opening 617 to the liquid channel 616. At the same time, the waste materials liquid, mixed with dead skin and other impurities, are collected by suction from the skin surface to the waste materials collection channels 619 and 620, and through the openings 618 and 621 to the tube 614 to the waste materials container. This dual-function plate is fixed onto the end of the skin treatment system by the plate holder 660, which has a groove channel 661, to be used to clip-on the plate to the mechanical coupling part by a flexible rubber ring. The suction strength can be adjusted based on the user comfortability level during skin exfoliation. This process will help in reducing the appearance of wrinkles, promote even skin tone, fight acne, shrink pores and improve the absorption of skincare products. The skincare products, provided simultaneously from the fluid channels 616, are designed in a way to facilitate uniform distribution of the skincare products during the application of the microdermabrasion procedure.

FIG. 14 illustrates an embodiment of the dual-function microdermabrasion plate 610, wherein the assembly of the new dual-function plate 640, shown in FIG. 14 is different in the structural design of the plate. The two major components, the diamond tips and the fluid supply and waste cleaning channels are overlapping in positions. The diamond tip particles 641 are fixed on the common base 646 and are arranged in a number of parallel lines, and the supply channel of the cleaning fluid 642 and the suction channels 643 of the waste materials are arranged between each two diamond tips lines. The supply of the cleaning fluids, healing cream, and skincare serums are provided from the containers of the fluids and the skin serum, through a flexible tube to the tube embedded into the dual-function plate 640, then through the openings 644 to the fluid channels 642. Providing the cleaning fluids and healing cream from the fluid supply channels 642 on the surface of the plate direct to the applicant skin, results in better skin exfoliation and faster healing time. This can help to maximize the results of the microdermabrasion process. At the same time, the waste fluids and the dead skin resulting from the microdermabrasion process are collected and removed by the continuous suction provided by negative pressure applied from the vacuum pump. The waste materials are collected and removed through the waste collection channels 643, then, through the opening 645 to the waste collection containers, through a number of fixed tubes embedded into the plate body, then through flexible tubes to the waste materials container. The cross-sectional view Y-Y of the dual-functional plate 640 is shown in FIG. 15.

Figure 15:
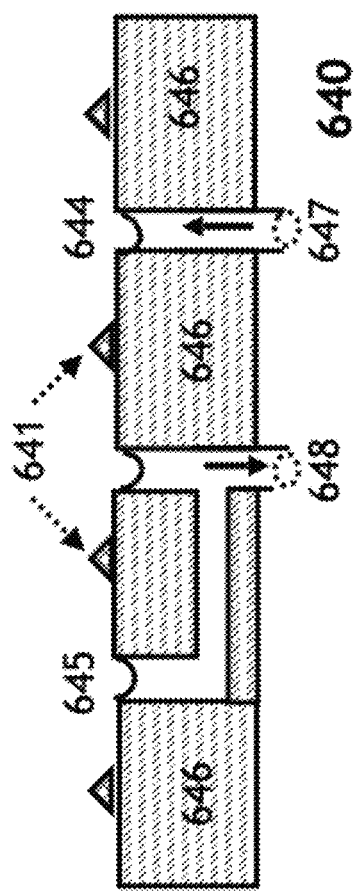
FIG. 15 is a schematic of the cross-sectional view Y-Y of the dual-function plate shown in FIG. 14.

FIG. 15 is a schematic of the cross-sectional view Y-Y of the dual-function plate 640 shown in FIG. 14. The figure shows the diamond tips 641 are fixed onto the top surface of the common base 646 in a spatial arrangement, while the supply of the cleaning fluids are pumped out of the liquids container and through the connecting tube 647, which is embedded into the common base 646 and through the opening 644 to the cleaning channel on the surface of the common base 646. At the same time, the waste materials, which are the remaining waste of the cleaning liquids and the dead skin resulting from the abrasion process, are moved by suction generated from the vacuum pump to the waste collection channels, then through the openings 645 to the fixed tubes 648 embedded into the common base 646 to the waste collection container.

Figure 16:
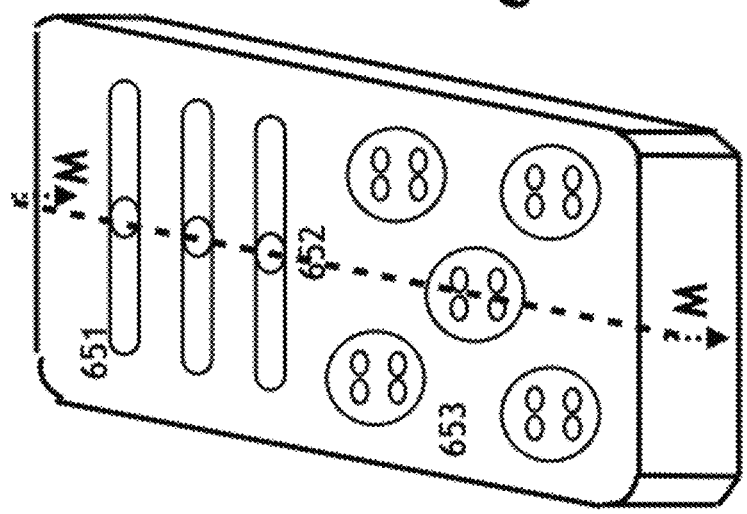
FIG. 16 shows a dual-function massaging plate having two main sections; one is shaped in a special curved surface for skin massaging, and the other section has a polarity of fluid channels in a special arrangement for continuous supply of serum and skin care products while the massaging process is conducted.

FIG. 16 shows an embodiment of the dual-function plate 610, wherein the dual-function plate 650 is used for skin massaging. The plate 650 has two main sections. One is shaped in special curvatures and solid bubbles 653 for skin massaging and improving blood circulation, while the other section has fluid channels 651 arranged in parallel positions for continuous supply of serum and skin care products during the massaging process. In every fluid channel there is an opening 652 connected to the serum container and skincare product container.

Figure 17:
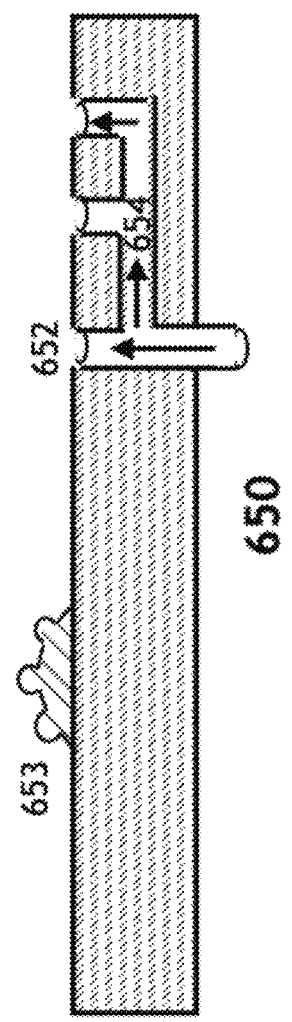
FIG. 17 is a schematic of the longitudinal cross-sectional view M-M of the dual-function massaging plate shown in FIG. 16.

FIG. 17 is a schematic of the longitudinal cross-sectional view M-M of the dual-function massaging plate 650 shown in FIG. 16. The surface of the plate is divided to two sides. The first side shows corrugations and curvatures with bubbles 653, which are used for skin massaging and more blood circulation. The other side shows the openings 652 centered in the fluid channels. These openings are connected through embedded tubes 654 to the serum supply containers.

Figure 18:
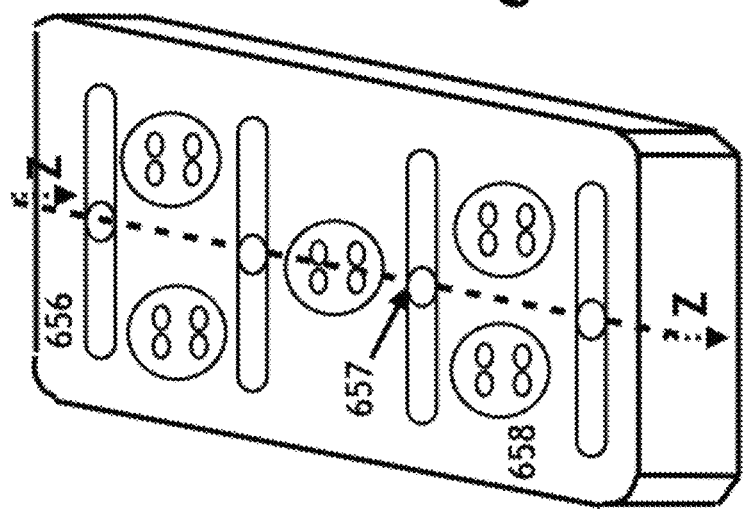
FIG. 18 shows an embodiment of the dual-function massaging plate shown in FIG. 16, wherein, the two main components of the plate, as the massaging curvature structure and the skincare supply channels are overlapping in a special arrangement on the surface of the dual-function plate.

FIG. 18 shows an embodiment of the dual-function massaging plate 650 shown in FIG. 16, wherein the plate 655 has the two main components, as the massaging curvature structure 658 and the skincare supply channels 656 are overlapping in a special arrangement on the surface of the dual-function plate 655. The solid curvature surface 658, which looks like bubbles on the surface of the dual-function plate 655, are used for skin massaging, while a supply of skincare cream and serum are continuously distributed on the surface of the skin. The skincare cream is pumped out of the liquid containers by air pressure from the mini vacuum pump and through flexible tubes to the opening 657 inside the supply channels 656 to the surface of the plate 655. The schematic of the longitudinal cross-sectional view Z-Z of the plate 655 is shown in FIG. 19.

Figure 19:
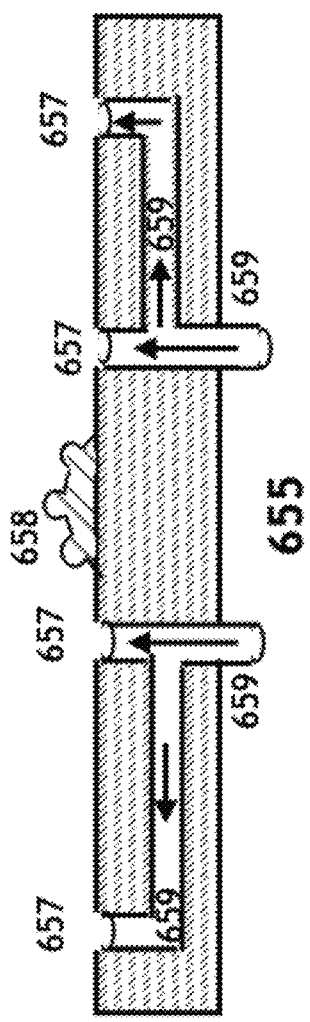
FIG. 19 is a schematic of the longitudinal cross-sectional view Z-Z of the dual-function massaging plate shown in FIG. 18.

FIG. 19 is a schematic of the longitudinal cross-sectional view Z-Z of the dual-function massaging plate, shown in FIG. 18. It shows in the center of the plate the cross-sectional view of one of the solid hemispherical structure 658, with a number of solid bubbles onto the surface, for skin deep massaging. Also, the figure shows the pipes 659 embedded into the plate body, which is used as a passage for the skincare products and serums pumped from the liquid containers in the base part of the system, to the liquid channels on the surface of the plate through the pipes 659 and openings 657. The plate is designed in a way to permit fluids or other materials to be transferred from the flexible tubes connected to the fluid containers to the fluid channels on the plate surface during the operation on the massage mode.

Figure 20:
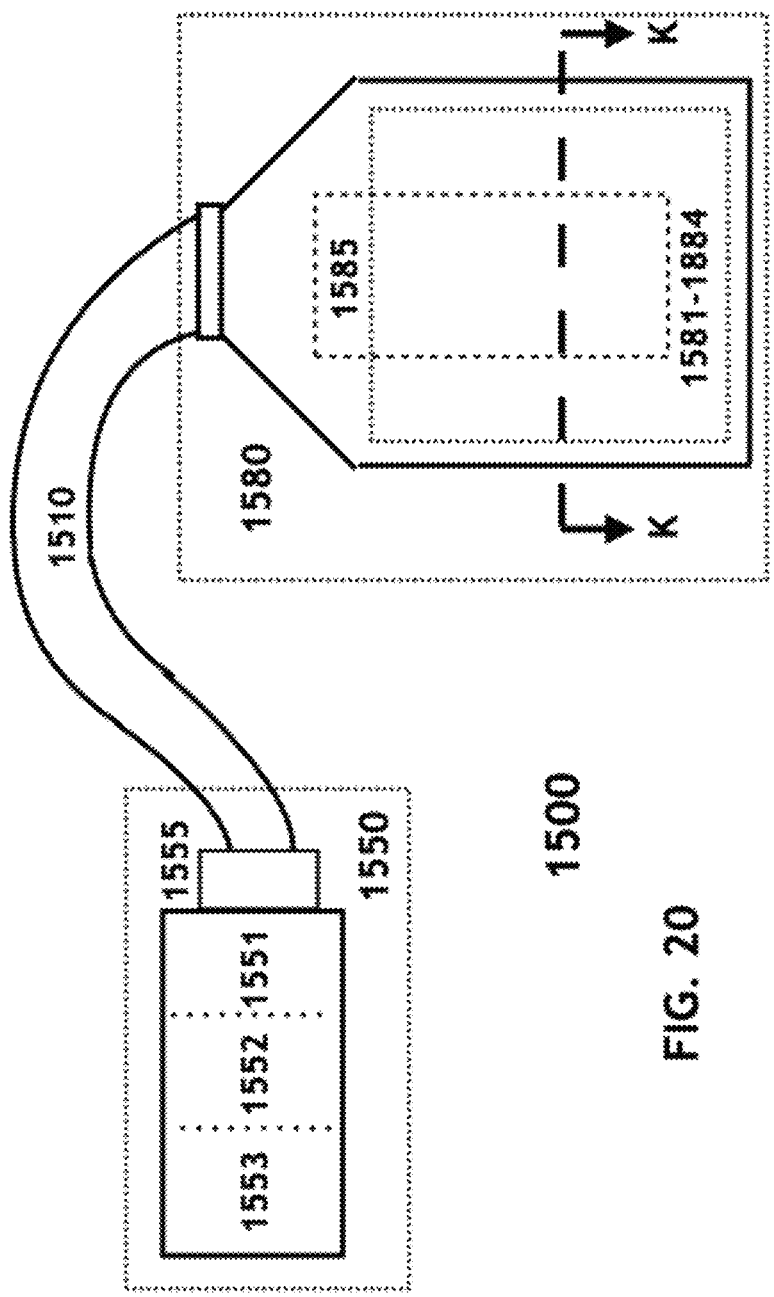
FIG. 20 shows an embodiment of the developed Universal Facial Rejuvenation Treatment System, wherein, the system is designed in two major parts (the target and the system base) connected together with a short flexible large size tube. This tube covers all the flexible small size tubes connecting the mini vacuum pump and containers in the base with the dual-function target/plate in the handheld part.

FIG. 20 shows another schematic of an embodiment of the developed Universal Facial Rejuvenation Treatment System 1500. This embodiment of the system 1500 is designed in two major handheld parts, wherein each part can be carried in one hand. The target part 1550 will be the moving part and light, while the system base part 1580, which is the heavy part, will be carried by the other hand, or on any stand in front of the operator. They are connected together with a short, flexible, large size tube 1510. This tube covers all the flexible small size tubes connecting the mini containers in the base 1580 with the dual-function plate 1553 in the head part 1550, through the plate holder 1552 and the coupling part 1551, and through a number of control switches and valves 1555. These switches and valves 1555 control the air suction pressure used in collecting waste materials when working in the microdermabrasion mode. Also, the switches and valves 1555 are used in controlling the flow of liquids passing from the liquid containers in the base part 1580 to the plate 1553, attached to the handheld part. The base part 1580 has two major groups of components. One group has all the containers 1581, 1582, 1583, 1584, which are used as reservoirs for the skincare supply and/or liquids, as well as a container for collecting waste materials. The second group 1585 has all the energy components, which include the mini vacuum pump, a set of rechargeable batteries, and an adaptor for connection to the electricity main supply. While the facial treatment system is small in size and light in weight for daily home use in general, in this new design, the moving part 1550 of the system will be small and extremely light for patients who can't handle the continuous movement of the system as one piece. The schematic cross-sectional view K-K of the base part 1580 is shown in FIG. 21.

Figure 21:
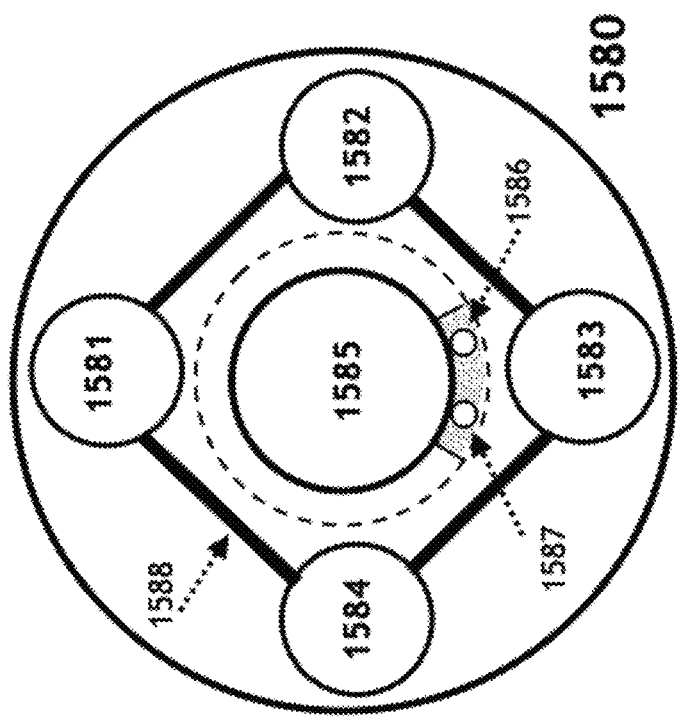
FIG. 21 is a schematic of the cross-sectional area K-K of the base part of the Universal Facial Rejuvenation Treatment System show in FIG. 20.

FIG. 21 shows a schematic of the cross-sectional view K-K of the base part 1580, of the embodiment Universal Facial Rejuvenation Treatment System 1500 show in FIG. 20. The figure shows the four containers 1581, 1582, 1583, 1584 used to save the skincare cream, serum and liquids, as well as a container to collect waste materials. These four containers are fixed in the body of the system and with respect to each other by a mechanical positioning structure 1588. The mini vacuum pump 1585 is located in the center area of the base part, and it is connected to the input and output air tubes 1586 and 1587, for circulating air pressure to liquid containers to push liquids or serum out of the container to the dual-function plates, and also for circulating negative pressure to the waste collection container to move waste liquids and dead skin from the skin surface to the waste collection container through waste collection channels in the surface of the dual-function plate. The base of the miniature system can be positioned on a counter or tabletop, while carrying the handheld part in hand during the treatment time. The connecting tube, between the base part and the handheld part, can be adjustable in length to match the space needed for easy handling of the system directly by the operator during use with all modes.

Figure 22:
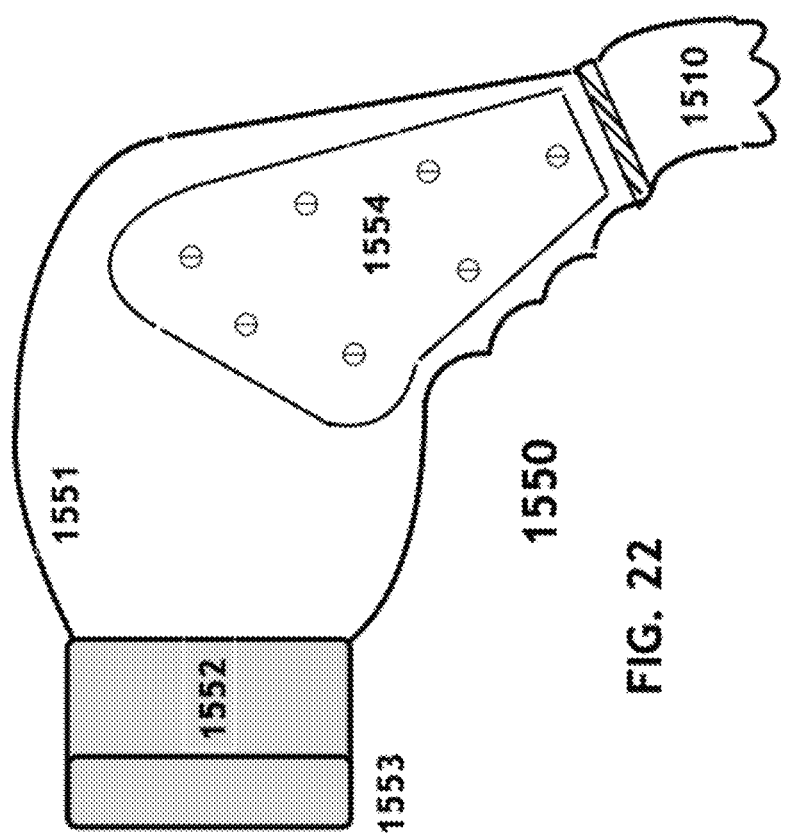
FIG. 22 shows the outer shape of the handheld part of the system shown in FIG. 20. The head part can be small and light for easy operation without carrying the entire system, while the base part can be on the counter or table a short distance away from the handheld part.

FIG. 22 shows a schematic of the outer shape of the handheld part 1550 of the system shown in FIG. 20, not to scale. The handheld part can be small in size and low in weight to allow for extended operation times with limited physical effort by the operator. This handheld unit is connected to system base through the large size tube 1510. The dual-function plate 1553 is connected to the body of the handheld part by the plate holder 1552, which is fixed to the body coupling part 1551. The body coupling part has a large size opening which is covered by a removable door 1554. This cover can be opened for maintenance and periodic service of the valves and switches within the handheld part of the system.

Figure 23:
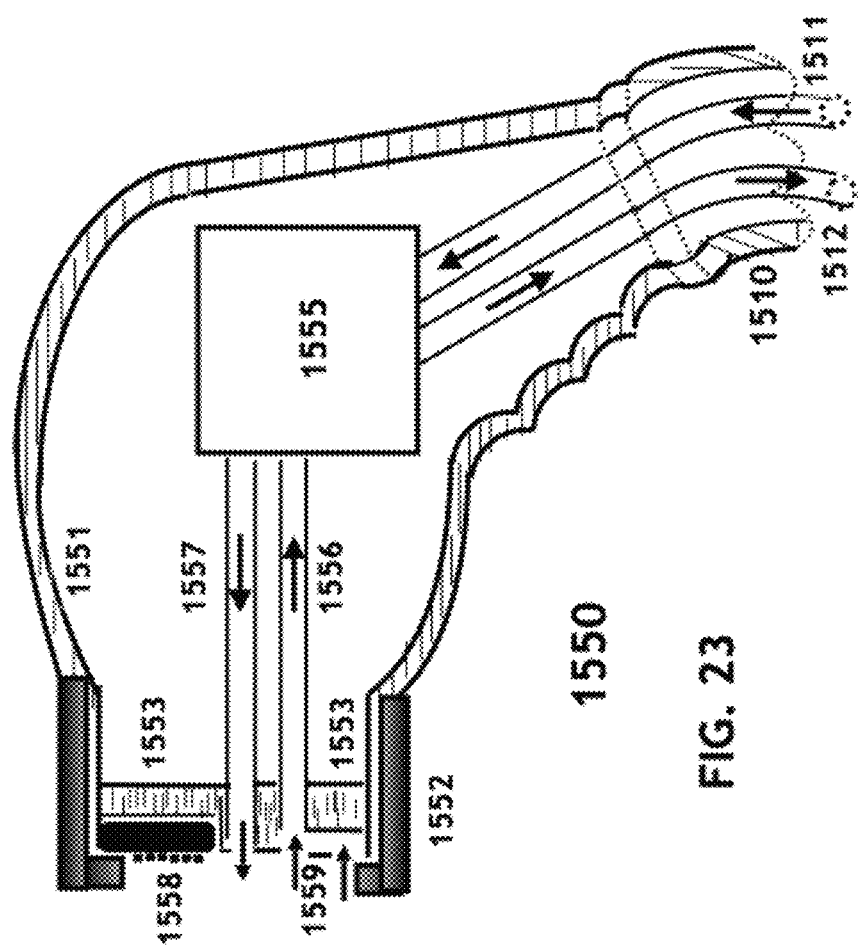
FIG. 23 is a schematic of the handheld part showing major components within this part.

FIG. 23 is a schematic of the handheld part 1550 of an embodiment of the disclosed skin treatment system showing major components within the structure of the system's handheld part. The mechanical coupling part 1551 is connected from one end to the large flexible holding tube 1510, and from the other end to the plate holder unit 1552. The large size flexible tube 1510 is used to connect the handheld part 1550 to the base of the system, and covers the flexible small size tubes 1511 and 1512, which carry liquids and skincare products from containers in the system base to the dual-function plate 1553 in the handheld part 1550, as well as removing waste materials from the plate surface to the waste collection container in the base of the system by suction and negative pressure generated by the miniature vacuum pump. The flow of the liquids and waste materials, which are moving by positive pressure or vacuum suction, are under full control by a set of valves and switches 1555 which are connected to the dual-function plate 1553 through flexible tubes 1556 and 1557. Those tubes 1556 and 1557 are connected to the waste collection channels and liquid channels, respectively, on the surface of the dual-function plate 1553. The dual-function plate has two major sections, the diamond tips section 1558 and the liquids supply channels and waste collection channels section 1559. This dual-function plate 1553 is connected to the mechanical coupling part 1551 by the plate holder 1552. The dual-function microdermabrasion plate 1553 can easily be removed and replaced with other plates, such as the micro-needling dual-function plate or the massaging and exfoliation dual-function plate, in order to service or treat other skin conditions.

Figure 24:
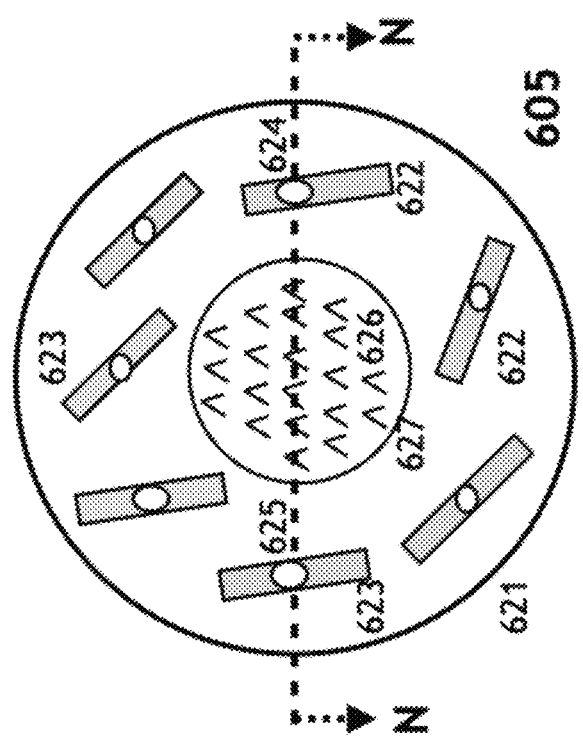
FIG. 24 is a schematic of an embodiment of the rectangular dual-function microdermabrasion plate shown in FIG. 13. Wherein the plate/disk is designed in a circular shape instead of the rectangular shown in FIG. 13. The diamond tips may be distributed uniformly around the center point of the circular plate, and the cleaning channels which supply the cleaning liquid and/or collect the dead skin, are covering the outer surface area of the circular dual-process plate.

FIG. 24 shows a schematic of an embodiment of the rectangular dual-function microdermabrasion plate 610, shown in FIG. 13. The plate 605 is designed in a circular shape instead of the rectangular shown in FIG. 13. Wherein the dual-function plate has two major sections 621 and 627. The first section 621 has all the liquid supply channels 622 and the waste collection channels 623. The liquid supply channels 622 has an opening 624 in each channel, which is connected to liquid supply containers. Also, each of the waste collection channels 623 has an opening 625 for continuous suction of waste liquids and dead skin removed from the skin surface to the waste collection container, by vacuum pressure induced from the mini vacuum pump. The second major section 627 of the dual-function plate 605, which has a large number of diamond tips distributed uniformly around the center point of the circular small plate 627. This small plate is surrounded by the cleaning channels, which are supplying the cleaning liquids, then collecting the waste liquids and dead skin continuously during skin treatment to maximize the skin healing conditions. The cross-sectional view N-N of the plate is shown in FIG. 25.

Figure 25:
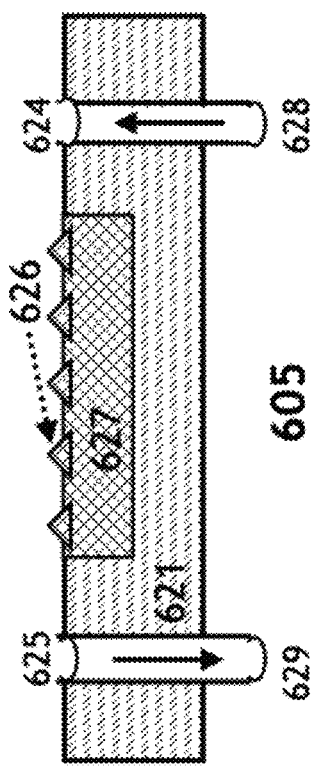
FIG. 25 is a schematic of the cross-sectional view N-N of the dual-function microdermabrasion plate shown in FIG. 24.

FIG. 25 is a schematic of the cross-sectional view N-N of the dual-function microdermabrasion plate 605 shown in FIG. 24. The two major sections of the plate are the 621 and 627. Section 621 has a number of liquid supply channels, wherein, each channel is connected through the opening 624 and the tube 628 to the liquid supply container. At the same time, each of the waste materials collection channels is connected through the opening 625 and the tube 629 to the waste materials collect container. The second major section of 627 is a small plate having a large number of diamond tips arranged in an efficient distribution for effective application of the microdermabrasion process.

While the invention has been described with reference to the embodiments above, a person of ordinary skill in the art would understand that various changes or modifications may be made thereto without departing from the scope of the claims.

We claim:

1. A handheld system for skin treatment, the system comprising;
    a plurality of dual-function plates, each dual-function plate being used for a specific skin treatment, wherein, each plate is capable of applying two compatible skin procedures simultaneously to maximize a skin response to the specific skin treatment;
    wherein a surface of each dual-function plate is subdivided into two sections, each section having required tools for application of one of the skin procedures;
    wherein a first section of the two sections is prepared for application of a skin treatment procedure, selected from a list consisting of: micro-needling, microabrasion, deep massaging, or another procedure, and a second section of the two sections has a plurality of fluid channels engraved into a surface of the dual-function plate to supply skincare products or to remove any waste materials on the surface of the dual-function plate;
    wherein fluids are saved in a number of mini containers, and a mini vacuum pump driven by a power supply is used to generate required air pressure to pump fluids from the number of mini containers, through a number of connecting tubes, to the plurality of fluid channels on the surface of the dual-function plate; and
    wherein waste materials and dead skin are collected from the surface of the dual-plate, by vacuum suction, through another number of connecting tubes to a waste collection container;
    wherein elements of the handheld system are integrated together in the handheld system;
    wherein the plurality of dual-function plates are configured to be used in a predetermined sequence for the skin treatment; and
    wherein one of the dual-function plates of the plurality of dual-function plates is configured for a skin micro-needling procedure as a micro-needling dual-function plate, wherein the first section of the two sections of the micro-needling dual-function plate includes a skin micro-needling roller and the second section of the two sections includes the plurality of fluid channels, wherein the plurality of fluid channels are engraved or built-in the plate surface that supply skincare products during the skin micro-needling procedure.

2. The system of claim 1, wherein the skin micro-needling roller is positioned between sides of the micro-needling dual-function plate in a free rotation condition wherein a plurality of micro-needles of 0.25 mm length, are fixed onto a cylindrical surface of the skin micro-needling roller in a predetermined arrangement for better interaction with skin tissue.

3. The system of claim 2, wherein the plurality of micro-needles on the cylindrical surface of the skin micro-needling roller are overlapping in position on the cylindrical surface of the skin micro-needling roller, wherein the plurality of fluid channels engraved into the cylindrical surface of the skin micro-needling roller distributes skincare fluids directly onto of the cylindrical surface of the skin micro-needling roller.

4. The system of claim 3, wherein skin treatment fluid is received in the plurality of engraved fluid channels through a plurality of pipes embedded inside the skin micro-needling roller to continuously supply skin treatment fluid while the skin micro-needling roller is rotating, to provide an approximately uniform distribution of the skin treatment fluid during the micro-needling procedure, wherein a skin treatment fluid supply is pumped from one of the number of mini containers to the plurality of pipes, to the plurality of engraved fluid channels into the cylindrical surface of the skin micro-needling roller through an opening inside each of the plurality of engraved fluid channels.

5. The system of claim 1, wherein the plurality of fluid channels are subdivided into two groups, a first group used to supply cleaning fluid from the fluid containers, and a second group is used in collecting the waste of the cleaning fluids and dead skin, and transport the waste and dead skin by suction from a mini-vacuum pump to the waste collection container.

6. The system of claim 1, wherein one of the plurality of dual-function plates has diamond tips and the plurality of engraved fluid channels are overlapping in positions and distributed uniformly across a surface area of one of the dual-function plates.

7. The system of claim 1, wherein one of the plurality of dual-function plates is used for deep massaging and skin health improvement, wherein the first section of one of the plurality of dual-function plates has surface corrugations and bubbles for skin deep massaging, and wherein some of the a plurality of fluid channels are used for supply of skin treatment fluids for better blood circulation and skin rejuvenation.

8. The system of claim 7, wherein one of the dual-function plates includes surface corrugations with bubbles and the plurality of fluid channels overlapping in positions and distributed uniformly across the dual-function plate surface.

9. The handheld system of claim 1, wherein the system is comprised within two handheld parts, wherein the two handheld parts are connected together with a number of flexible tubes, wherein the plurality of dual-function plates is within a first part that is a head part and the remainder of the elements of the system are with a second part of the system, wherein the head part is configured for movement over the skin surface.

10. The system of claim 1, further comprising switches and valves that provide control and/or adjusting of the air pressure for fluids moving from the number of mini containers to the surface of the dual-function plate and the vacuum suction for moving the waste materials and dead skin from the surface of the dual-function plate to the waste collection container.

11. The system of claim 1, further comprising a dual-function plate holder that connects any of the plurality of dual-function plates to a body of the system through a coupling piece engaged to the body of the system and the dual-function plate holder, wherein the coupling piece configured to use a clip-on technique to achieve engagement.

\* \* \* \* \*